US012687493B2

(12) United States Patent
Jansen et al.

(10) Patent No.: US 12,687,493 B2
(45) Date of Patent: Jul. 21, 2026

(54) ALIGNMENT-TOLERANT PHOTONIC SENSING SYSTEM

(71) Applicant: IMEC VZW, Leuven (BE)

(72) Inventors: Roelof Jansen, Heverlee (BE);
Jeonghwan Song, Heverlee (BE)

(73) Assignee: Imec vzw, Leuven (BE)

( * ) Notice: Subject to any disclaimer, the term of this patent is extended or adjusted under 35 U.S.C. 154(b) by 456 days.

(21) Appl. No.: 18/516,527

(22) Filed: Nov. 21, 2023

(65) Prior Publication Data

US 2024/0210318 A1     Jun. 27, 2024

(30) Foreign Application Priority Data

Dec. 21, 2022    (EP) ..................................... 22215684

(51) Int. Cl.
*G01N 21/64*          (2006.01)
*G01N 33/542*        (2006.01)

(52) U.S. Cl.
CPC ....... *G01N 21/6428* (2013.01); *G01N 33/542* (2013.01)

(58) Field of Classification Search
CPC ............. G01N 21/6428; G01N 21/553; G01N 21/6454; G01N 21/65; G01N 21/7703; G01N 21/6452; G01N 21/648; G01N 33/542
See application file for complete search history.

(56) References Cited

U.S. PATENT DOCUMENTS

| | | | |
|---|---|---|---|
| 2013/0203627 A1* | 8/2013 | Moll ................. | G01N 21/7703 |
| | | | 506/18 |
| 2016/0341895 A1 | 11/2016 | Bienstman et al. | |
| 2019/0187162 A1* | 6/2019 | Shastry ................. | G01N 21/13 |
| 2021/0215607 A1* | 7/2021 | Berman .............. | G01N 21/648 |

(Continued)

FOREIGN PATENT DOCUMENTS

| | | | |
|---|---|---|---|
| CH | 708389 A2 * | 1/2015 | ....... G01N 33/54373 |

OTHER PUBLICATIONS

Machine Translation of CH 18516527 A2 (Year: 2023).*

(Continued)

*Primary Examiner* — Michael L Hobbs
(74) *Attorney, Agent, or Firm* — McDonnell Boehnen Hulbert & Berghoff LLP

(57)          ABSTRACT

Example embodiments relate to alignment-tolerant photonic sensing systems. An example sensing system includes an illumination module for delivery of a light beam. The sensing system also includes a cartridge that includes a photonic sensor chip having a length axis and a width axis. The photonic sensor chip includes a plurality of grating couplers in a first areal portion of the photonic sensor chip. The photonic sensor chip also includes a plurality of sensing sites. Additionally, the photonic sensor chip includes waveguides connecting each grating coupler to a respective sensing site or group of sensing sites of the plurality of sensing sites. Further, the sensing system includes a cartridge holder for releasably receiving and locking the cartridge into a sensing position. The photonic sensor chip is aligned relative to the illumination module up to permitted alignment tolerances when the cartridge is locked into the sensing position.

20 Claims, 3 Drawing Sheets

(56)　　　　　References Cited

U.S. PATENT DOCUMENTS

2022/0229053 A1　　7/2022　Levin et al.

OTHER PUBLICATIONS

Extended European Search Report and Search Opinion, Application No. EP 22215684.6, mailed May 16, 2023, 11 pages.

Martens, Daan, Genghua Dong, and Peter Bienstman. "Optimized Si3N4 grating couplers for relaxed alignment requirements under flood illumination." Applied Optics 56, No. 5 (2017): 1286-1290.

Martens, Daan, Patricia Ramirez-Priego, Mohammed Shariff Murib, Ayssar A. Elamin, Ana Belén González-Guerrero, M. Stehr, F. Jonas et al. "A low-cost integrated biosensing platform based on SiN nanophotonics for biomarker detection in urine." Analytical methods 10, No. 25 (2018): 3066-3073.

Werquin, Sam, Diedrik Vermeulen, and Peter Bienstman. "Implementation of surface gratings for reduced coupling noise in silicon-on-insulator circuits." IEEE Photonics Technology Letters 26, No. 16 (2014): 1589-1592.

Janz, S., D-X. Xu, M. Vachon, N. Sabourin, P. Cheben, H. McIntosh, H. Ding et al. "Photonic wire biosensor microarray chip and instrumentation with application to serotyping of Escherichia coliisolates." Optics express 21, No. 4 (2013): 4623-4637.

Arce, C. Lerma, E. Hallynck, S. Werquin, Jan-Willem FIB Hoste, D. Martens, and p. Bienstman. "Silicon photonics biosensing: different packaging platforms and applications." In Microfluidics, BioMEMS, and Medical Microsystems XIII, vol. 9320, pp. 20-25. SPIE, 2015.

Carlborg, Carl Fredrik, Kristinn Björgvin Gylfason, Andrzej Kaźmierczak, Fabian Dortu, MJ Bañuls Polo, A. Maquieira Catala, Gerhard M. Kresbach et al. "A packaged optical slot-waveguide ring resonator sensor array for multiplex label- free assays in labs-on-chips." Lab on a Chip 10, No. 3 (2010): 281-290.

Estevez, M. Carmen, Mar Alvarez, and Laura M. Lechuga. "Integrated optical devices for lab-on-a-chip biosensing applications." Laser & Photonics Reviews 6, No. 4 (2012): 463-487.

Bhatta, D., M. B. McDonnell, and E. Perkins. "Multiplexed detection of biological agents using optical microchip sensors." In Optics and Photonics for Counterterrorism and Crime Fighting VI and Optical Materials in Defence Systems Technology VII, vol. 7838, pp. 285-291. SPIE, 2010.

* cited by examiner

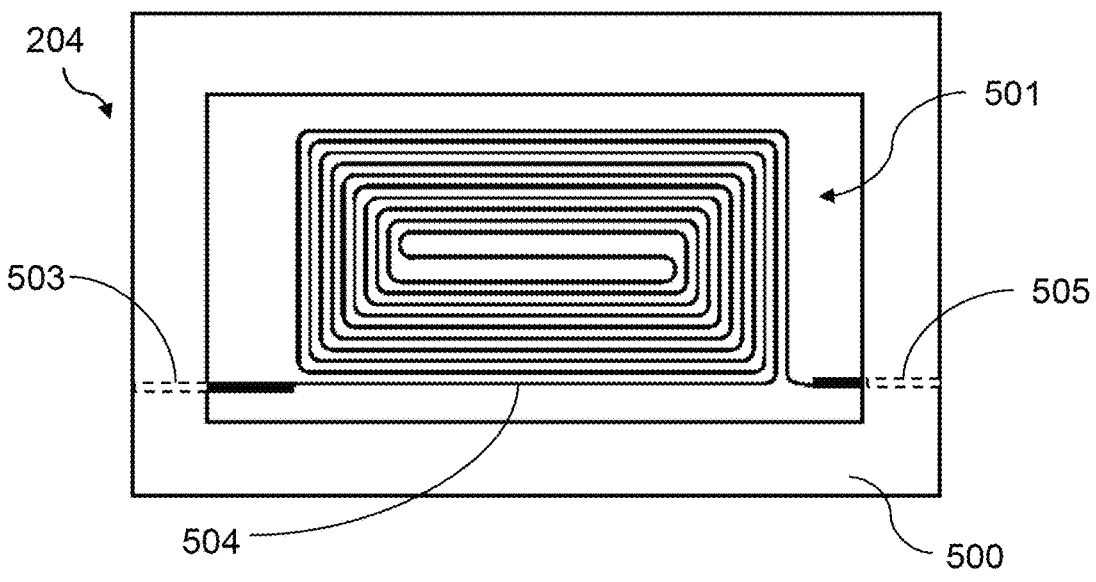
FIG. 5
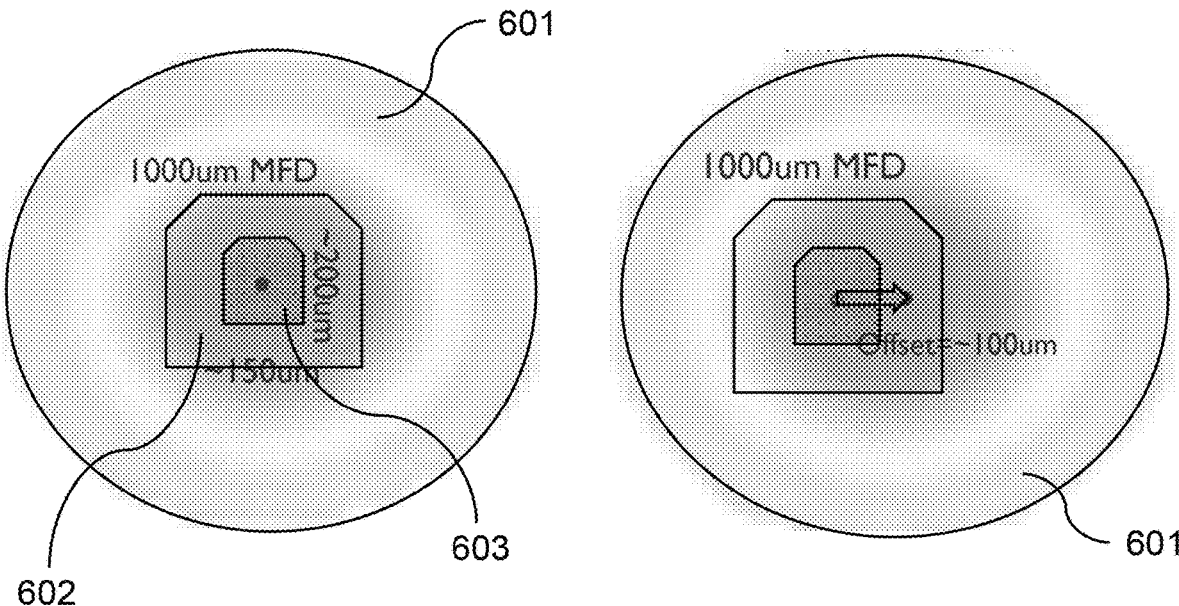
FIG. 6A          FIG. 6B

ALIGNMENT-TOLERANT PHOTONIC SENSING SYSTEM

CROSS-REFERENCE TO RELATED APPLICATIONS

The present application is a non-provisional patent application claiming priority to European Patent Application No. EP 22215684.6, filed Dec. 21, 2022, the contents of which are hereby incorporated by reference.

FIELD OF THE DISCLOSURE

The present disclosure generally relates to photonic sensing systems that contain a carrier for the on-chip photonic sensor and an illumination source as separate components, and particularly relates to photonic sensing systems that provide for relaxed alignment constraints of the illumination source relative to the on-chip photonic sensor.

BACKGROUND

Bio-photonic sensor chips are increasingly becoming of interest in the field of point-of-care diagnostics at affordable prices. The integration of bio-photonic sensor chips onto microfluidic cartridges has spurred the development of disposable cartridges. The on-chip integration of inexpensive light sources that are suitable for bio-sensing applications is challenging from a technological standpoint, thus delaying a cost-effective mass-manufacturability and a widespread dissemination of these sensor chips. Meanwhile, disposable cartridges that are designed to co-operate with dedicated illumination and optical readout units—typically assembled into a housing of the sensing system—are a promising alternative.

In Lerma Arce, Cristina, et al. "Silicon Photonics Biosensing: Different Packaging Platforms and Applications." MICROFLUIDICS, BIOMEMS, AND MEDICAL MICROSYSTEMS XIII, vol. 9320, SPIE-INT SOC OPTICAL ENGINEERING, 2015, a sample collection tube is described, which is glued onto the front side of a biophotonic sensor chip. The bio-photonic sensor chip is hold in place by a vacuum chuck and illuminated from the back-side. Light that is coupled into the bio-photonic sensor chip is guided towards a plurality of sensing sites, where waveguides are contacting a fluid sample provided in the collection tube. This allows the light in the waveguides to interact with the fluid sample at the respective sensing sites. An image sensor is used to optically read out the output signals bio-photonic sensor chip.

The proposed assembly has the disadvantage that the bio-photonic sensor chip needs to be manually placed onto the chuck; a positioning method that lacks the accuracy and repeatability necessary for automatic or semi-automatic analysis. Moreover, the bio-photonic sensor chip may accidently be moved in the plane of the chuck. To ensure that enough input light is coupled into the bio-photonic sensor chip before and during the time the sensing operation is carried out, the bio-photonic sensor chip needs to be aligning carefully with respect to the illumination source. The alignment process may need to be repeated several times before the sensing operation starts and constantly verified as long as the sensing operation is being performed. This can be a time-consuming burden, especially when different fluid samples on different bio-photonic sensor chips have to be analyzed and placed successively onto the chuck. Another disadvantage is that reaction tubes first have to be glued onto the sensor chips, which leads to assembled parts that are bulky and fragile.

SUMMARY

Example embodiments may provide photonic sensing systems in which the alignment of the photonic sensor chip relative to the light source may be less demanding. For example, some embodiments provide photonic sensing systems that are straightforward to handle and have relaxed alignment requirements.

In one aspect, the present disclosure relates to a sensing system. The sensing system sensing system includes an illumination module for light beam delivery, a cartridge which includes a photonic sensor chip, and a cartridge holder that releasably receives the cartridge and locks it to a sensing position. The photonic sensor chip has a length axis and a width axis. The photonic sensor chip includes a plurality of grating couplers in a first areal portion thereof, a plurality of sensing sites, and waveguides connecting each grating coupler of the plurality of grating couplers to a respective sensing site or group of sensing sites of the plurality of sensing sites. When the cartridge is locked into the sensing position, the photonic sensor chip is aligned relative to the illumination module up to permitted alignment tolerances, which include at least a permitted amount of longitudinal and lateral misalignment along the length and width axis of the photonic sensor chip respectively. The permitted amounts of longitudinal and lateral misalignment define a peripheral portion of the photonic sensor chip which surrounds the first areal portion. The illumination module is arranged to project the light beam onto the photonic sensor chip, whereby a second areal portion of the photonic sensor chip is illuminated. When the sensor cartridge is locked into the sensing position, the second areal portion fully includes the first areal portion and at least partly includes the peripheral portion.

The sensing system may be used, for instance, in biomedical sensing applications or gas sensing applications. As the illuminated region of the photonic sensor chip completely overlaps and extends beyond the areal region of the photonic sensor chip that is occupied by the input grating couplers, lateral and longitudinal alignment tolerances can be relaxed.

In some embodiments, the alignment process of cartridges with photonic sensor chips relative to an illumination module in sensing system assemblies may be user-friendly and require only a low level of expertise, or no expertise at all.

In some embodiments, different or same cartridges can be repeatedly inserted and removed from the sensing system without any significant loss of alignment accuracy. Locked into the sensing position, inserted cartridges are ready for use; this saves time that the user does not have to spend on accurately positioning the photonic sensor chip and verifying the working conditions of the cartridge and photonic sensor chip.

In some embodiments, cost-effective, mass-manufacturable cartridges and photonic integrated circuits can be used in combination with pre-mounted reliable light sources. A costly on-chip integration of light sources can thus be avoided as well as excessive costs for system assembly and maintenance due to overly tight alignment tolerances. Separating the illumination module from the photonic sensor chip also provides more flexibility in the optical design of the illumination beam path. Optical filters, beam shaping components, or other optical elements may be removably positioned into the beam path to enhance functionality of the sensing system or seamlessly adapt to the cartridge types of different vendors and different photonic integrated circuit technologies.

The present disclosure also relates to a biomedical apparatus that includes the sensing system of the first aspect.

Particular aspects are set out in the accompanying independent and dependent claims. Features from the dependent claims may be combined with features of the independent claims and with features of other dependent claims as appropriate and not merely as explicitly set out in the claims.

For purposes of summarizing example embodiments, certain aspects have been described above. Of course, it is to be understood that not necessarily all such aspects may be achieved in accordance with any particular embodiment. Thus, for example, it is understood that embodiments may be carried out in a manner that includes one aspect as taught herein without necessarily including other aspects as may be taught or suggested herein.

The above and other aspects will be apparent from and elucidated with reference to the embodiment(s) described hereinafter.

BRIEF DESCRIPTION OF THE DRAWINGS

Example embodiments will now be described further with reference to the accompanying drawings.

FIG. 5 illustrates a sensing site of the photonic sensor chip, according to example embodiments.

FIG. 6A illustrates the spatial overlap of irradiated second areal portion and input grating coupler array in the first areal portion of the photonics sensor chip under perfect alignment conditions when the cartridge with photonic sensor chip is locked into the sensing position, according to example embodiments.

FIG. 6B illustrates the spatial overlap of irradiated second areal portion and input grating coupler array in the first areal portion of the photonics sensor chip with a permitted lateral offset condition when the cartridge with photonic sensor chip is locked into the sensing position, according to example embodiments.

Figures 1, 2:
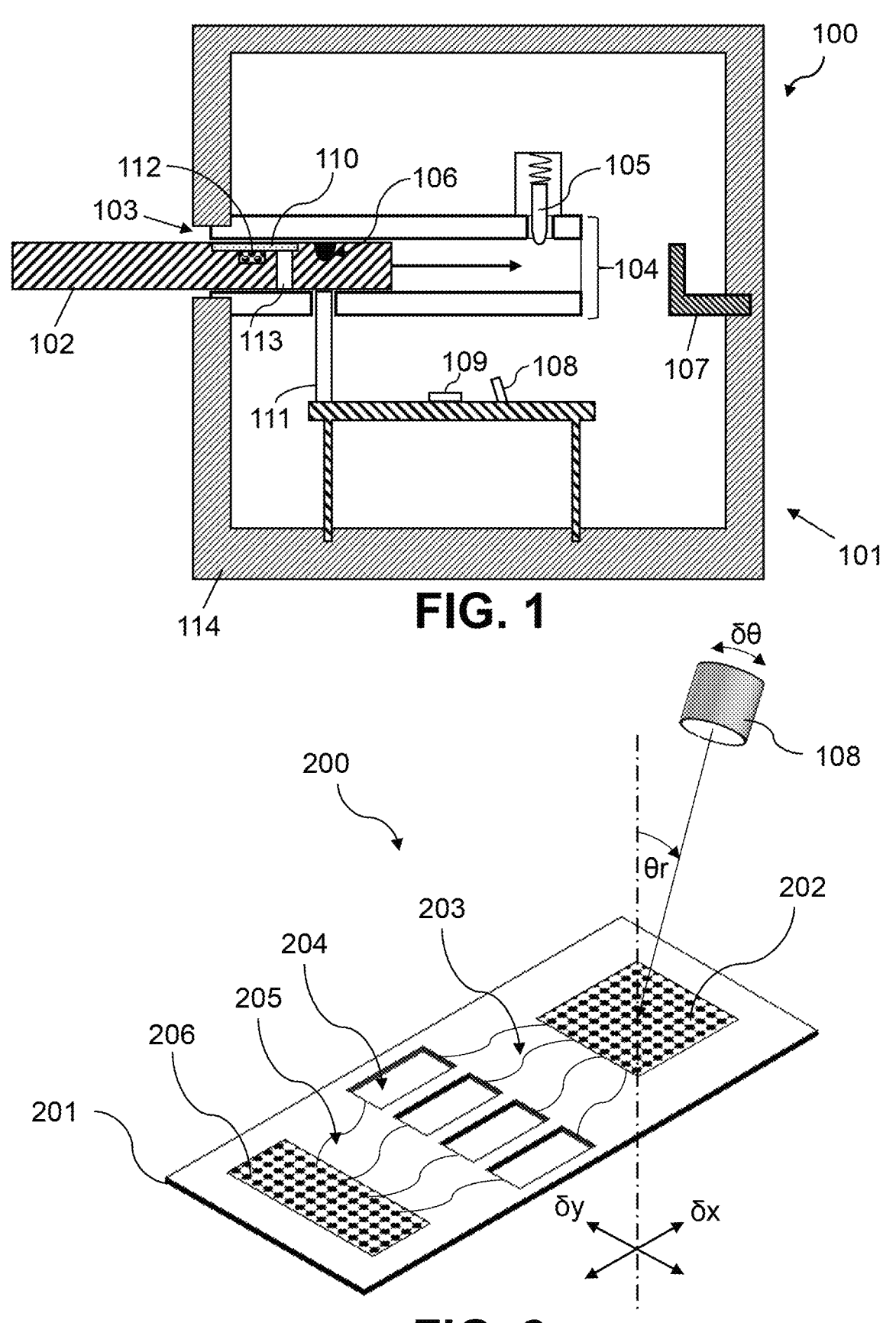
FIG. 1 is a cross-section through a sensing system, according to example embodiments.
FIG. 2 is a perspective view of a photonic sensor chip in the sensing position and illuminated by a light beam delivered by the illumination module, according to example embodiments.

The drawings are only schematic and are non-limiting. In the drawings, the size of some of the elements may be exaggerated and not drawn on scale for illustrative purposes. The dimensions and the relative dimensions do not necessarily correspond to actual reductions to practice.

Any reference signs in the claims shall not be construed as limiting the scope.

In the different drawings, the same reference signs refer to the same or analogous elements.

DETAILED DESCRIPTION

The present disclosure will be described with respect to particular embodiments and with reference to certain drawings, but the invention is not limited thereto.

Directional terminology such as top, bottom, front, back, leading, trailing, under, over, and the like in the description and the claims is used for descriptive purposes with reference to the orientation of the drawings being described, and not necessarily for describing relative positions. Because components of example embodiments can be positioned in a number of different orientations, the directional terminology is used for purposes of illustration only, and is in no way intended to be limiting, unless otherwise indicated. It is, hence, to be understood that the terms so used are interchangeable under appropriate circumstances and that the example embodiments described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B.

Reference throughout this specification to "one embodiment" or "an embodiment" means that a particular feature, structure or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures or characteristics may be combined in any suitable manner, as would be apparent to one of ordinary skill in the art from this disclosure, in one or more embodiments.

Similarly it should be appreciated that in the description of example embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment.

Furthermore, while some embodiments described herein include some but not other features included in other embodiments, combinations of features of different embodiments are meant to be within the scope of the disclosure, and form different embodiments, as would be understood by those in the art.

In the description provided herein, numerous specific details are set forth. However, it is understood that embodiments may be practiced without these specific details. In other instances, well-known methods, structures, and techniques have not been shown in detail in order not to obscure an understanding of this description.

When reference is made to the light coupling efficiency value for a particular grating coupler, what is meant is the ratio of incident power of the beam illuminating a surface of the photonic sensor chip that includes that grating coupler to power of the fraction of light of the illuminating beam that is effectively coupled into the photonic sensor chip by that grating coupler. Given that a broad beam for illumination of the photonic sensor chip creates a large spot size on the surface of the photonic sensor chip that includes that grating coupler, larger than the grating coupler itself, the light coupling efficiency value tends to be relatively small. Not because of excessive losses, but due to the mismatch between illumination spot size and grating coupler dimension.

FIG. 1 is a schematic cross-section through a sensing system 100 according to example embodiments. The sensing system 100 includes a cartridge 102 and an analysis tool 101 as separate components. An illumination module 108, a readout module 109, and a fluid pump arrangement 111 are also assembled inside the analysis tool 101. The sensing system may be part of a biomedical sensing apparatus. However, embodiments are not limited to biomedical sensing applications but may be used in different sensing applications, for example gas sensing. In the latter case, the fluid would be a gas or a gas mixture.

The cartridge can be slidably inserted, in the direction of its length axis, through a slot opening 103 in the analysis tool housing 114. To assist the user with the cartridge insertion process, the shape and dimension of the slot opening may match the shape and dimension of the cartridge when viewed along the longitudinal/length axis. A cartridge holder includes or is assembled from guide rails 104, one or more alignment pins 105, and a stopping member or rear alignment pin 107. Guide rails 104 are a non-limiting example of guiding means that are suitable to direct the cartridge motion through the slot opening 103 and towards a sensing position of the cartridge in the analysis tool. The guide rails maintain the cartridge at a fixed height throughout the insertion process. A spring-loaded alignment pin 105 is arranged alongside the guide rails and configured to releasably engage a corresponding indention 106 formed on a major surface of the cartridge. Engaged, the spring-loaded alignment pin 105 locks the cartridge 102 into a sensing position relative to the illumination module 108. Although only a single alignment pin is shown in FIG. 1, at least two alignment pins may be provided to properly locate the cartridge with respect to the illumination module, when the cartridge is moved to the sensing position. Additionally, a stopping member or rear alignment pin 107 may be provided to prevent users from inadvertently pushing the cartridge too far into the analysis tool, which could cause damage to the cartridge or components in the interior of the analysis tool.

Other suitable locking means including clamps, latches, or brackets may be used. For instance, the analysis tool according to another embodiment can be provided with a cartridge carrier assembly that uses spring-biased hooks as latches which hold secure the cartridge to the cartridge carrier assembly. The cartridge carrier assembly itself may be mounted onto the frame of a motorized linear positioning stage, which moves the cartridge into the sensing position after the cartridge has been secured to the cartridge carrier assembly A photonic integrated circuit (PIC), hereinunder referred to as photonic sensor chip 110, is lodged into a recess on a major surface of cartridge 102. A plurality of sensing sites on the photonic sensor chip 110 allow for light-matter interactions between light propagated along the photonic sensor chip and a biological sample on, over or in direct in contact with the sensing sites of the photonic sensor chip, thereby lending biosensing functionality to the sensor chip. Input grating couplers are provided on the surface of the photonic sensor chip that is facing the illumination module 108 and arranged to couple a beam of light emitted by the illumination module into the photonic sensor chip, when the cartridge is locked into the sensing position. In some embodiments, the input grating couplers are arranged as one-dimensional or two-dimensional grating coupler array. The input grating couplers each couple a portion of the light beam received from the illumination module into a corresponding waveguide of the photonic sensor chip. These waveguides propagate and distribute the coupled portions of light in the plane of the photonic sensor chip and deliver the coupled light portions to the sensing sites of the photonic sensor chip. In general, each input grating coupler is associated with and supplies light to one sensing site, or one group of sensing sites of the plurality of sensing sites, and there is one waveguide connected between each input grating coupler and its corresponding sensing site, or group of sensing sites. If a waveguide supplies a group of sensing sites, a light splitting structure (e.g. directional coupler tree, multimode interference coupler/coupler tree) divides the waveguide into a plurality of secondary feed waveguides that deliver in-coupled light to the different sensing sites of the group of sensing sites. The sensing sites belonging to a group of sensing sites that is fed by one and the same input grating coupler are thus illuminated in parallel. In some embodiments, the light splitting structure divides the input light equally amongst all connected secondary feed waveguides. At the sensing sites, the coupled light portions interact with a sample and optical response signals are collected in the waveguides. Light output couplers, e.g. output grating couplers, which are configured to couple the collected response signals out of the photonic sensor chip, are connected to the waveguides traversing the sensing sites and project the out-coupled response signals towards the readout module 109, when the cartridge is locked into the sensing position.

In some embodiments, the biological samples is a fluid sample containing fluorophores as bio-markers. In this case, the coupled light portions are in the visible wavelength region (e.g. 635 nm) and excite the fluorophores in the fluid sample that is flown past the sensing sites, e.g. through evanescent field coupling. The fluorescence light (e.g. 600-750 nm) is then collected as a response signals in the waveguides that traverse the sensing sites. An optical bandwidth (e.g. the 3 dB or 10 dB full width at half maximum (FWHM) bandwidth) of the output grating couplers may accommodate the fluorescence spectrum. However, example embodiments are not limited to fluorescence-based biosensing applications. Other light-matter interactions may be explored and the sensing sites adapted accordingly. For instance, response signals may correspond to an attenuated portion of the coupled light that is incident at one or more sensing sites, thus providing information regarding the light absorption characteristics by the biological sample. Biological samples, or biological species in the sample, may also be identified using nonlinear spectroscopy, e.g. nonlinear Raman spectroscopy. The collected response signals then carry information on the Raman scattering behavior of the sample instead of representing an absorption or fluorescence profile.

The cartridge includes a microfluidic delivery system, e.g. a fluidic system including fluid inlet and fluid outlet ports, fluidic channels communicating with the fluid inlet and outlet ports, e.g. via fluidic valves, and optionally storage chambers such as blister pouches that can store the bio-markers for onboard delivery. The microfluidic delivery system may be entirely formed on the cartridge, e.g. molded into the cartridge material, and may be composed of one or more communicating layers. In some embodiments, the cartridge is made from bio-compatible disposable material such soft polymers, e.g., polydimethylsiloxane (PDMS). Alternatively, the cartridge can be made from silicon directly, which has the benefit of being manufacturable at wafer scale.

Embodiments are not concerned with the particularities of the microfluidic delivery system as long as it provides a suitable interface to the photonic sensor chip. An adequate interface between the microfluidic delivery system of the cartridge and the photonic sensor chip may include at least one microfluidic channel 112 or at least one microfluidic sensing chamber which is formed on or over the waveguides at the location of the sensing sites. By way of example, a sensing area may be defined as the portion of each waveguide that passes through or passes under a microfluidic channel or microfluidic chamber. The interaction length may be increased if the waveguides follow a meandering or spiraling path at the sensing sites. A cladding layer of the waveguides may be removed locally at the sensing sites, thereby enabling a direct contact between the waveguide and the biological samples flow across the so exposed waveguide area. Microfluidic channels may be partially opened along one of their sides or provided with holes in order to establish a fluid interface between the microfluidic delivery system and the photonic sensor chip. The microfluidic delivery system of the present embodiment has fluid inlet and outlet ports that are aligned with and provide fluidic communication with a fluid pump arrangement 111 and fluid exhaust arrangement respectively. The fluid pump arrangement may include one or more controllable fluid injection devices such as controllable plungers or syringe pumps. In the field of biomedical sensing, the fluid to be delivered is an aqueous solution in general.

The substrate of the cartridge may be removed locally at its backside, e.g. on the other major surface opposite to the major surface that carries the photonic sensor chip, to obtain an optical port 113 that facilitates illumination and readout of the photonic sensor chip. In some embodiments, the optical port 113 enables free space illumination between the illumination module 108 and the photonic sensor chip 110, whereby reflective or scattering objects or surface on the light path are avoided. In some embodiments, the optical port 113 also enables free space propagation of optical response signals between the photonic sensor chip 110 and the (external) readout module 109 (not an issue for on-chip integrated readout modules). This has the benefit that the illumination intensity on the light-coupling surface of the photonic sensor chip can be maintained at a high level without requiring the illumination module to output a brighter light beam. Moreover, stray light in the analysis tool can be minimized.

In some embodiments, the illumination module 108 includes a coherent light source. Suitable coherent light sources may be a laser diode, a vertical-cavity surface-emitting laser (VCSEL), etc. The illumination module may include a collimator, e.g. a collimator lens or lens train, which provides a more directional illumination of the photonic sensor chip, i.e. light beam supplied by the illumination module that is less divergent, e.g. substantially parallel, when being projected onto the light-coupling surface of the photonic sensor chip. The collimator may act upon a more divergent beam of light delivered by the coherent light source, e.g. the more divergent light cone exiting an optical fiber of a fiber-coupled laser or the more divergent light cone exiting a waveguide facet of an edge-emitting laser. The power of the light beam emitted by the illumination module may in the range of several mW, e.g. below 500 mW, e.g.

less than 100 mW. Hence, coherent light sources may be used in the illumination module without addition of an optical amplification device and without being cooled. In some embodiments, light may be delivered with optical power in the 0.1-1.0 μW range to each sensing site of the photonic sensor chip; optical power values that are sufficient to collect a measurable amount of response light signals such as fluorescence signals from each sensing site. A light output power of the illumination module in the range of several mW may be sufficient even for very small coupling efficiency (CE) values of the individual input grating couplers, e.g. CE values lower than –20 dB, e.g. between –30 dB and –40 dB. Moreover, the intensity and/or wavelength of the light beam emitted by the illumination module may be adjustable, e.g. via current modulation and/or temperature modulation of the coherent light source.

The light beam emitted by the illumination module may be linearly polarized along the sensitive coupling direction of the grating couplers on the photonic sensor chip when the cartridge is locked into the sensing position, e.g. polarized along the prominent direction of polarization (TE or TM) of the grating couplers. In some embodiments, the input grating coupler array may be polarization diverse, i.e., include grating couplers of a first and second kind, respectively having TE-polarization and TM-polarization as their prominent polarization direction. Optionally, the illumination module may include beam shaping optical components which determine the spatial profile of the light beam projected onto the light-coupling surface of the photonic sensor chip. This allows, for instance, a Gaussian-shaped output beam to be transformed into a flat-top or elliptically shaped output beam.

The readout module 109 is arranged to detect the response light signals coupled out of the photonic sensor chip 110, e.g. via surface output grating couplers as light emitters, when the cartridge is locked into the sensing position. Suitable readout modules 109 may include a one-dimensional or two-dimensional detector array, e.g. a one-dimensional or two-dimensional photodiode array, image sensor or camera. Image-forming optics or collection optics may be part of the readout module 109 and relay an image of the light emitters on the photonic sensor chip to the detector array. It is possible to have the detector array of the readout module co-integrated on the photonic sensor chip, in which case the response signals can be coupled out of the signal collection waveguides and directly into the photodetection elements of the integrated detector array. In this way, additional image-forming optics or collection optics may not be needed.

In alternative embodiments, the response light signals are coupled out of the photonic sensor chip via edge couplers, in which case the detector array may be attached to or positioned alongside a lateral or longitudinal edge of the photonic sensor chip. In yet other embodiments, the readout module and the illumination module are combined into a single unit, for instance through a shared objective that uses beam-splitting optics to separate the light paths of the illumination module and the readout module. Additional optical filters may be positioned in the light path of the readout unit, e.g. to filter or block reflected light from the coherent light source at the illumination wavelength and/or to separate the spectrum of the response light signals from the input spectrum of the coherent light source in the readout path.

In some embodiments, the response signals from the different sensing sites are detected as independent output signals by the readout module, e.g., are detected in different regions of a two-dimensional image sensor or are detected by different photodetectors or a detector array. This allows for a multiplexed readout of the optical response signals obtained from the plurality of sensing sites, e.g., multiplexed sensing at faster output signal acquisition rates and higher throughput. Reading out the response signals from each sensing site (sensing channel) separately may allow different sensing strategies or more complete sensing strategies to be pursued in parallel. For instance, different reagents, different biological control agents and/or different light-matter interaction lengths (sensing lengths) can be explored in parallel in order to analyze different components of the biological sample and/or obtain separate fits for the response signal and an optical loss (e.g. waveguide and coupling losses) affecting the response signal. Besides, one or more sensing sites may sense a background signal and their optical response signals may be used as reference or control signals that characterize the sensor status/sensor conditions.

In alternative embodiments, the detected response signals are combined, e.g. summed or averaged, by the readout module to obtain a stronger total output signal or an output signal with an improved signal-to-noise ratio from the plurality of sensing sites. This may be achieved in the analog domain in hardware, e.g. by binning the individual photo-detection elements of the detector array, or in the digital domain, e.g. through digital signal post-processing. Alternatively, an integrating sphere or large-area photodetector may be used to combine the collected response signals from the individual sensing sites into an aggregate output signal. A large-area photodetector may be bonded onto a light-outcoupling surface of the photonic sensor chip, e.g. over-laying and collecting response light from a plurality of surface output grating couplers. Combining the response signals into an aggregate output signal may allow the output signal to be largely independent of changes in the illumination conditions of the photonic sensor chip when there is some tolerated amount of misalignment between the cartridge in the sensing position and the illumination module.

Although the present embodiment shows the illumination module 108, the readout module 109, and the fluid pump arrangement 111 mounted onto a same mounting plate, these components may be mounted onto different supports or assembled differently in the analysis tool. In a variant of the present embodiment, the illumination module 108 and the readout module 109, for instance, are arranged in such a way as to illuminate and detect optical response signals from a front side of cartridge (upwards facing side of the cartridge in FIG. 1 that has the recess for receiving the photonic chip). The photonic sensor chip would then have to be flipped around before lodging it into the receiving recess on the front surface of the cartridge. The respective positions of the illumination module 108, the readout module 109 and the fluid pump arrangement 111 may be pre-calibrated in the analysis tool so that optical illumination, optical readout and fluid supply is achieved when the cartridge is locked into the sensing position. It is noted that the mechanical alignment and pre-calibration of these components may be conducted by the manufacturer of the analysis tool and the user is not allowed to have, or does not need to have, direct access to these components. This ensures that the initial alignment and pre-calibration is not altered inadvertently by the user.

FIG. 2 is a perspective view of the photonic sensor chip under illumination conditions when the cartridge (not shown) carrying the photonic sensor chip is in the sensing position. The photonic sensor chip 200 has a plurality of surface grating input couplers 202 formed on a major surface of the sensor chip substrate 201, e.g. a layered silicon nitride—silicon oxide—silicon substrate with silicon nitride being used as the waveguide core layer. This major surface extends in a longitudinal direction (x) of the cartridge and a lateral direction (y) of the photonics sensor chip. The plurality of surface grating input couplers 202 may be arranged into an array in a first areal portion on the major surface of the photonic sensor chip 200. Each surface grating input coupler couples a portion of the light beam that is emitted by the illumination module 108 and received on the first areal portion. Light distributing waveguides 203 (only a few shown) connect each input coupler to a corresponding sensing site 204. They deliver the respective portions of the light beam that are coupled into the photonic sensor chip as input light to the sensing sites, where the delivered input light is transduced into optical response signals through interaction with a biological sample. Light collecting wave-guides 205, which are connected to or an extension of the light distributing waveguides 203, capture the optical response signals at the sensing sites and guide the captured response signals to a plurality of surface grating output couplers 206, which are also formed on the substrate major surface. At the sensing sites 204, a cladding layer of the light distributing and light collecting waveguides 203, 205 is removed to locally expose the waveguides to the biological sample.

Optionally, one or more of the waveguides that connect the input grating couplers to the corresponding sensing sites or group of sensing sites are adapted to couple a small fraction of guided light to a power monitor. Faulty cartridges or cartridges that cannot be properly aligned/locked into position can be detected through missing or incoherent signals generated at the power monitor outputs. The user can be informed accordingly. Additionally, the power monitors can be used to detect power imbalances of in-coupled light across the plurality of input grating couplers, e.g., across the array of input grating couplers. The optical response signals collected at the respective sensing sites can then be inter-preted in the light of the detected level of optical power that is input to the sensing site. This facilitates the isolation of the signal components in the gathered response signals that are attributable to the light-matter interaction events such as fluorescence photon emission events, inelastic Raman scattering events, etc.

The illumination module 108 emits a beam of light at a reference angle "Or" with respect to a surface-normal direction of the photonic sensor chip, e.g. orthogonal to the x-direction and the y-direction in the present embodiment. The reference angle may correspond to the illumination angle of the grating coupler at which light of a predeter-mined illumination wavelength may be coupled into the light distributing waveguides of the photonic sensor chip. Upon projection onto the photonic sensor chip, the light beam supplied by the illumination module 108 forms a light spot which irradiates a second areal portion on the major surface of the photonic sensor chip. The sensing sites should be excluded from the second areal portion, unless they are insensitive to out-of-plane light at the major surface of the photonic sensor chip, e.g., through an opaque light shield or a light-absorbing or light-reflecting layer that does not interfere with the intended sensing operation. In some embodiments, a centre location of the first areal portion containing the plurality of input grating couplers is spatially aligned with a centre location of the second areal portion, i.e. a centre location of the projected light beam, when the cartridge is locked into the sensing position. Here, a centre location of the projected light beam is defined as the barycentre/centre of gravity of the light spot (i.e. the first moments of the x-coordinate and the y-coordinate, considering the intensity distribution of the light spot as a probability density function) formed on the photonic sensor chip when the cartridge is locked to the sensing position. It is a characteristic variable of the light beam that can be obtained by experimental measurement with a beam profiler set up to record a two-dimensional intensity distribution at similar illumination conditions as for the photonic sensor chip (e.g. same angle of incidence, same distance to the illumination module). The centre location of the first areal portion can be defined as the geometrical centre of the convex hull that contains the plurality of input grating couplers.

Given the imperfections and mechanical tolerances of the cartridge holder, the uncertainties related to the mounting position and mounting angles of the pre-calibrated illumination module in the analysis tool assembly, and the uncertainty related to the photonic sensor chip position on the cartridge, the resulting alignment of the cartridge relative to the illumination module is not perfect when the cartridge is locked into the sensing position, and is not perfectly repeatable when the same or a different cartridge is again inserted into the analysis tool and moved to the sensing position. It is thus meaningful to define the sensing position of the cartridge relative to the illumination module up to a permitted range of alignment tolerances, e.g. allowing for a pre-determined amount of lateral misalignment "δ y" and a predetermined amount of longitudinal misalignment "δ x" with respect to a reference position of perfect alignment (or zero misalignment). As described above, this reference position of perfect alignment may correspond to coinciding centre locations of the first and second areal portion of the photonic sensor chip. In some embodiments, the permitted range of alignment tolerance will also accommodate a predetermined amount of angular misalignment "δ θ" of the angle of incidence, i.e. the angle formed between the propagation direction of the light beam emitted by the illumination module and the sensor chip's surface-normal direction. In practice, alignment tolerances of +/−100 μm along the longitudinal and lateral axis, and an angular tolerance of +/−1° may be used.

As a result of lateral and/or longitudinal misalignment, the illuminated second areal portion of the photonic sensor chip tends to shift relative to the first areal portion containing the input grating couplers, causing an offset between the respective centre locations of the first and second areal portion. Embodiments may provide remedy misalignment and offsets between the areal portion of the photonic sensor that contains the input grating couplers and the areal portion of the photonic sensor that is illuminated by the illumination module of the analysis tool when the cartridge with photonic sensor chip is locked into the sensing position. This may include selecting or adapting an illumination module so that it delivers light beams with a sufficiently large beam size (e.g. large beam waist or large mode field diameter) so that the illuminated second areal portion of the photonic sensor chip encompasses and surrounds the first areal portion of the photonic sensor chip, thereby allowing for lateral and longitudinal misalignment of the cartridge with photonic sensor chip relative to the illumination module. In some embodiments, a dense packing of the input grating couplers in the first areal portion is provided so that a large number of input grating couplers, feeding a corresponding large number of multiplexed sensing sites, fits in the first areal portion. A dense packing of the input grating couplers in the first areal portion may also help obtain a higher total amount of light coupling into the photonic sensing chip; that is, a sum of the small coupling efficiency values of the individual input grating couplers across the first areal portion can still be optimized for a given light beam profile.

Figure 3:
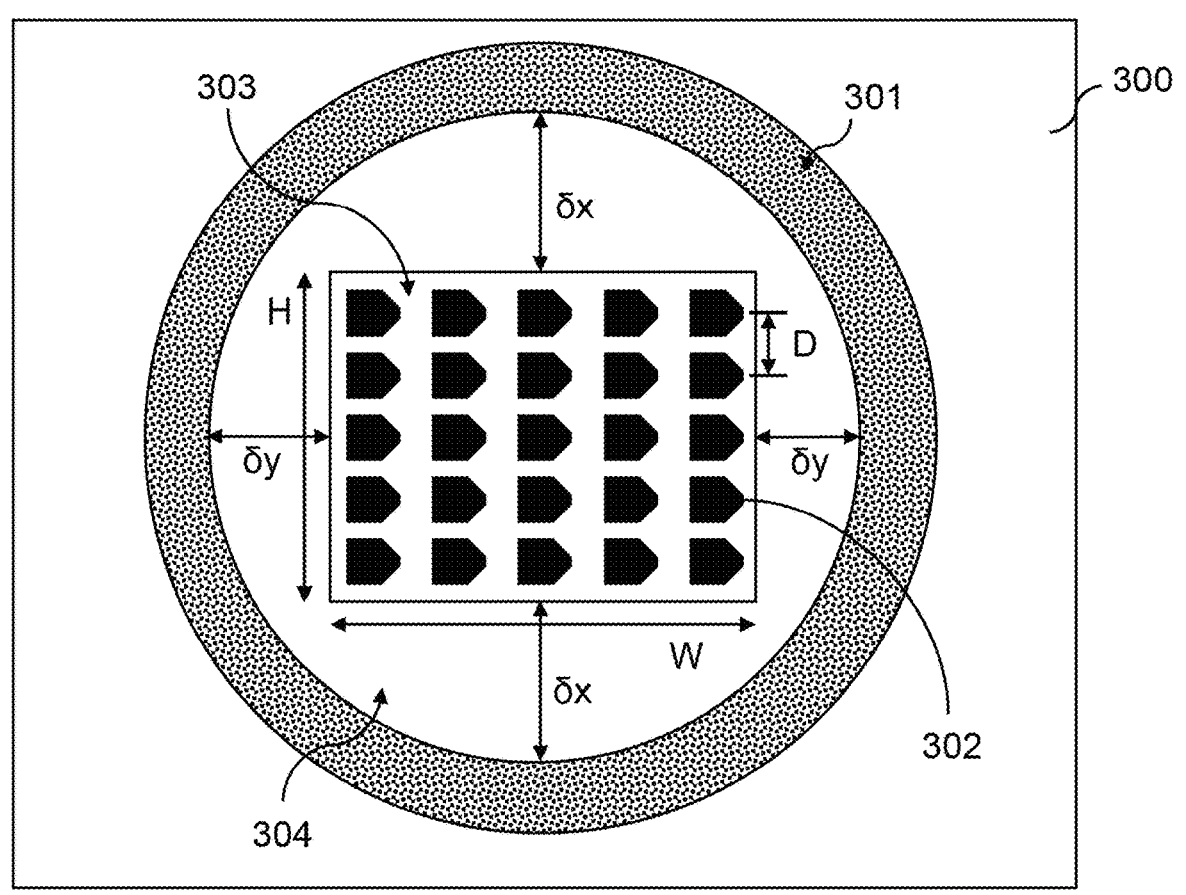
FIG. 3 shows an illuminated part of a photonic sensor chip and the relationship between first and second areal portion of the photonic sensor chip, when the cartridge is locked in the sensing position, according to example embodiments.

FIG. 3 shows an illuminated part of a photonic sensor chip according to example embodiments and further explains the relationship between first and second areal portion of the photonic sensor chip when the cartridge is locked in the sensing position. An array of input grating couplers 302 is located in and occupies a first areal portion 303 of the photonic sensor chip 300, e.g. on a major surface thereof. This array of input grating couplers 302 extends over a width "W" in the lateral direction and over a height "H" in the longitudinal direction of the cartridge and photonic sensor chip 300. Some values of the height and width are H=20 . . . 1000 μm and W=20 . . . 1000 μm, respectively (e.g., H=50 . . . 500 μm and W=50 . . . 500 μm). Adjacent input grating couplers of the array are separated by a distance "D", which is the smallest centre-to-centre distance between neighbouring grating couplers. In some embodiments, this distance "D" is of the same order as the smallest dimension of an individual input grating coupler of the array, and the gap between adjacent input grating couplers of the array is smaller than the smallest dimension of an individual input grating coupler of the array. Mode field diameters which match the size of the individual input grating couplers of the array would partially overlap in the gap region between adjacent input grating couplers. This allows a dense packing of input grating couplers in the array, yielding a high fill factor over the first areal portion.

The first areal portion 303 forms the convex hull of the array of input grating couplers 302. Consequently, the outer perimeter of the first areal portion delimits the array of input grating couplers at its periphery (outer boundary). Although displaying a rectangular shape, the array of input grating couplers 302 and the corresponding first areal portion 303 of the photonic sensor chip are not limited to a particular shape. In alternative embodiments, the array of input grating couplers and the corresponding first areal portion of the photonic sensor chip may display, for instance, a polygonal shape.

The light beam that is received from the illumination module forms a light spot on the photonic sensor chip, e.g. on a major surface thereof. This light spot illuminates a second areal portion 301 of the photonics sensor chip 300, which overlaps and completely surrounds the first areal portion when the cartridge with photonic senor chip is in the sensing position. For regular beam profiles with a single intensity peak, e.g. Gaussian, super-Gaussian or Lorentzian beam profile, or homogeneous beam profiles, e.g. flat-top beam profile, the second areal portion is generally defined by the projected peak location and the diameter or waist of the light beam. The beam diameter is defined either as the full width at half minimum or as the $1/e^2$-width (i.e. mode field diameter) with respect to the peak intensity value. Alternatively, the second areal portion can be defined as an ellipse whose lateral and longitudinal extent on the photonic sensor chip are determined by the second moments of the x-coordinate and the y-coordinate respectively, considering the intensity distribution of the light spot as a probability density function. This latter definition also includes highly irregular and/or non-homogeneous beam profiles, as well as light beams that have different diameters along different principal axis, e.g. an elliptical light beam having a first principal diameter in the lateral direction of the photonic sensor chip and a second principal diameter in the longitudinal direction of the photonic sensor chip. Commercially available beam profilers can be used to determine the second areal portion experimentally.

In the present embodiment, the second areal portion has a circular shape or slightly elliptical, which may be expected for a light beam having a Gaussian beam profile and incident at small reference angles "θr", e.g. about θr=8°. However, embodiments are not limited to circularly or elliptically shaped second areal portions. For instance, a nearly rectangularly shaped second areal portion of the photonic sensor chip may be illuminated. Illumination beams with higher-order transverse modes, such as higher-order transverse modes of Gaussian-Hermite beams, Gaussian-Laguerre beams or Bessel beams may be used to create homogeneously illuminated second areal portions on the major surface of the photonic sensor chip. This may be beneficial in sensing applications in which different sensing sites use light supply with different power levels, e.g., accounting for different losses, geometries, sensitivities and/or reagents at the different sensing sites.

As indicated in the drawing, the second areal portion 301 also includes, completely or partially, a peripheral portion 304 of the photonic sensor chip. The peripheral portion is directly adjacent to and surrounds the first areal portion. It forms a band-like circumferential region around the first areal portion: an alignment tolerance band. This alignment tolerance band accounts for positional changes of the first areal portion relative to the centre of the second areal portion, provided these positional changes fall within the permitted range of lateral and/or longitudinal misalignment. The width of the tolerance band at either side of the first areal portion reflects the predetermined range of permitted amounts of lateral and longitudinal misalignment. In the present embodiment, the peripheral portion 304 has a circular or elliptical shape. The peripheral portion 304 extends over a distance δ y from each horizontal boundary of the first areal portion/input grating coupler array, and also extends over a distance δ x from each vertical boundary of the first areal portion/input grating coupler array. Example distances δ x and δ y range from 10 μm to 1000 μm (e.g., from 20 μm to 500 μm, such as 20-200 μm or 100-300 μm).

In some embodiments, the peripheral portion is the intersection of a scaled version of the first areal portion and the first areal portion itself, wherein scale factors (greater than unity) along the longitudinal and lateral direction of the photonic sensor chip may be different, e.g. when the permitted alignment tolerances along the longitudinal and the lateral direction are different.

Figure 4:
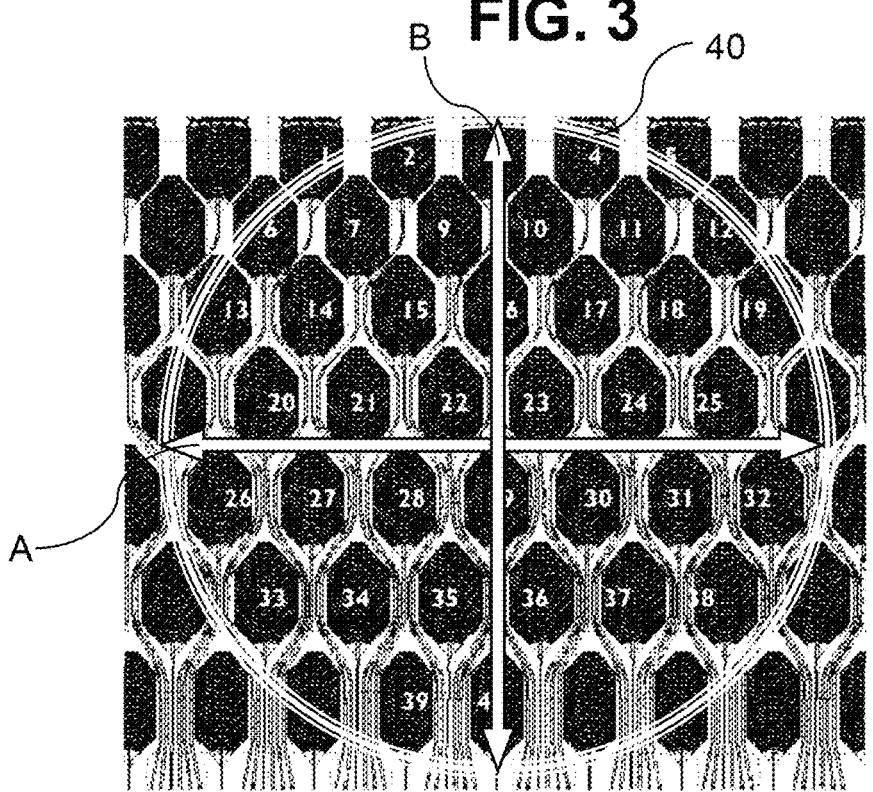
FIG. 4 illustrates an arrayed configuration of a plurality of input grating couplers, according to example embodiments.

FIG. 4 shows an arrayed configuration of a plurality of input grating couplers, according to example embodiments. Forty input grating couplers are arranged on a hexagonal lattice with substantially elliptical perimeter 40. This perimeter delimits a first areal portion on a major surface, e.g. upper surface, of the photonic sensor chip. The first major axis "A" of the elliptical perimeter 40, oriented parallel to the width (lateral) axis of the photonic sensor chip, measures about 140 μm. The second major axis "B" of the elliptical perimeter 40, oriented parallel to the length (longitudinal) axis of the photonic sensor chip, measures about 180 μm. Each input grating coupler of the array has a footprint of 14 μm*14 μm and connects via a 10-15 μm long taper to a light distributing waveguide. Adjacent grating couplers of the array are separated by a 5 μm wide gap, allowing a high fill factor and dense spatial packing of grating couplers in a first areal portion of the photonic sensor chip. This may allow a large number of input grating couplers to be illuminated in parallel and with relaxed angular tolerances, thus enabling multiplexed sensing at a large number of sensing sites. Moreover, high aggregate/total light coupling efficiency of the array can be obtained. Here, the total coupling efficiency of the array is defined as the sum of the individual coupling efficiencies of all the grating coupler composing the array. The light in-coupling efficiency of the input grating couplers can be further improved, e.g. by providing a bottom reflector below the cladding layer underneath the grating teeth etched into the waveguide core layer, but is always lower than a reference coupling efficiency value reported in respect of a mode-matched illumination beam (i.e., an illumination beam whose mode field diameter is approximately equal to the dimensions of the individual grating coupler). A number of grating teeth associated with each one of the plurality of grating couplers may be in the range from thirty to sixty.

The light in-coupling efficiency of individual input grating couplers of the illuminated grating coupler array ranges from −60 dB to −10 dB, e.g., from −40 dB to −20 dB, in some embodiments. A variance in the coupling efficiency values across the plurality of grating couplers is at most 10 dB in the absence of lateral and longitudinal misalignment, e.g., in the 0.1-10 dB range, such as in the 0.1-3 dB range. A relative change in total coupled power related to the plurality of grating couplers in the presence of lateral and/or longitudinal misalignment is less than 10.0%, e.g., less than 1.0%.

The forty light distributing waveguides feed forty sensing sites (multiplexed). In order to sense the same biological sample in the same manner and under similar conditions, all the sensing sites may contact one and the same microfluidic channel or sensing chamber. The optical response signals collected at the sensing sites are guided towards an array of output grating couplers, matching in number with the sensing sites. Compared to the array of input grating couplers, the outline of the output grating coupler array is subjected to less stringent alignment tolerances, especially if a large-area photodetector is used in the readout module. By way of example, the forty output grating couplers may be organized into a 5*8 array, occupying an area of 300*240 μm². Adjacent output grating couplers may be separated by at least 20 μm wide gaps. Individual output grating couplers may have more compact dimensions, but longer tapers than their counterparts in the input-sided array; e.g. a 10*10 μm² footprint and at least 20 μm long tapers. The more compact design of the output grating couplers compared to the input grating couplers allows for a broader spectral bandwidth. This is beneficial for the efficient outcoupling of broadband fluorescence response signals.

In some embodiments, the main dimension (i.e. largest dimension) of the second areal portion may be two to ten times bigger than the main dimension of the first areal portion, e.g. two to five times bigger, e.g. two or three times bigger. An increase in the size of the second areal portion at constant size of the input grating couplers and first areal portion, e.g. through an increase in the mode field diameter of a Gaussian beam, leads to even more tolerant alignment ranges and better uniformity of the grating's coupling efficiencies across the array, but decreases the total optical power coupled by the grating coupler array. Alternatively, changing the beam profile from a Gaussian shape to a flat-top beam has the similar effect of enlarging the alignment tolerance ranges and improving the uniformity of coupling efficiencies across the grating coupler array.

FIG. 5 shows a sensing site of the photonic sensor chip according to example embodiments. A cladding layer 500 for waveguides in the plane of the photonic sensor chip is locally removed in a sensing window 501, thus exposing a spiral waveguide 504 to a biological sample when flown across the sensing site 204. The spiral waveguide 504 connects the light distributing waveguide 503 to the light collecting waveguide 505. An example size of the sensing window 501 bounding the spiral waveguide 504 may be 450 μm*300 μm in a silicon nitride on insulator photonics technology platform and the sensing length associated with the spiral waveguide 504 may be 1.5 cm. Up to forty sensing sites or more can be multiplexed on a single photonic sensor chip of size 4*4 mm².

FIGS. 6A and 6B show the spatial overlap of irradiated second areal portion 601 and input grating coupler array in the first areal portion 603 of the photonics sensor chip under perfect alignment conditions (FIG. 6A) and for a permitted lateral offset of approximately 100 μm (FIG. 6B) when the cartridge with photonic sensor chip is brought into the sensing position. In this embodiment, the input grating coupler array has a size of 150*200 μm² and includes 40 surface grating couplers patterned into a silicon nitride-based waveguide core layer surrounded by silicon oxide cladding layers. Each input grating coupler includes 30 grating teeth and is substantially square-shaped with a footprint of about 14*14 μm². Adjacent grating couplers of the array are separated by a 4 μm wide gap.

The light beam for illumination of the second areal portion 601 has a Gaussian profile and a $1/e^2$-diameter of 1000 μm. This relatively large beam diameter ensures that the second areal portion 601 encloses the first areal portion 603 as well as a peripheral portion 602 of the photonic sensor chip which is surrounding the first areal portion. The peripheral portion 602 is concentric with the first areal portion 603 (i.e. same center of gravity) and is defined through a 100 μm wide circumferential tolerance band along the outer perimeter of the first areal portion. This alignment tolerance band thus accounts for shifts in the location of the first areal portion relative to the center of the second areal portion within the permitted range of lateral and/or longitudinal misalignment, in this case +/−100 μm along the horizontal and the vertical axis. The width of the tolerance band reflects the predetermined range of permitted amounts of lateral and longitudinal misalignment. As illustrated in FIG. 6B, even in the event of a lateral offset of 100 μm, the second areal portion is still encompassing the first areal portion and the entirety of the peripheral portion. In other embodiments, the tolerance band can be selected as wide or wider than the largest dimension of the first areal portion. Wider tolerance bands also lead to wider peripheral portions of the photonic sensor chip, which may cause partial overlap between the second areal portion and the peripheral portion for some permitted values of lateral and/or longitudinal misalignment.

A coupling efficiency value for the light beam portion that is coupled by a single grating coupler at the center of the first areal portion (without bottom reflector) amounts to −34.43 dB under perfect alignment conditions. This coupling efficiency value decreases only insignificantly to −34.77 dB when the first and second areal portion are laterally offset by 100 μm, which demonstrates the design robustness and design capability to tolerate misalignment. Likewise, the non-uniformity of coupling efficiency values across the array is less than 1.0 dB for situation (a) and only increases slightly to 1.5 dB for situation (b). The present photonic sensor chip design further tolerates an angular misalignment of about +/−1.0° (angular FWHM-bandwidth). The aggregate coupling efficiency of all the grating couplers of the array is about 1.4% under perfect alignment conditions (a) and only drops by an insignificant amount of 0.1% under lateral misalignment conditions (b). This equals a relative change in the aggregate coupling efficiency of approximately 7%; well below a relative change of 10% that is generally achievable in some embodiments.

Sizing the grating couplers in the embodiment of FIGS. 6A and 6B twice as large, e.g. 28*28 μm² and using 60 grating teeth, roughly doubles the aggregate coupling efficiency (3.0%) and the first areal portion (350*400 μm²), but diminishes the angular alignment tolerance to +/−0.5°. Moreover, the coupling efficiency values of single grating coupler at the center of the first areal portion (without bottom reflector) in this case amounts to −29.8 dB for situation (a) and −30.2 dB for situation (b). The relative change in the aggregate coupling efficiency reduces to approximately 3%

While example embodiments have been illustrated and described in detail in the drawings and foregoing description, such illustration and description are to be considered illustrative and not restrictive. It will be appreciated, however, that no matter how detailed the foregoing appears in text, embodiments may be practiced in many ways. Other variations to the disclosed embodiments can be understood and effected by those skilled in the art in practicing the claimed invention, from a study of the drawings, the disclosure and the appended claims. Any reference signs in the claims should not be construed as limiting the scope.

What is claimed is:

1. A sensing system comprising:
an illumination module for delivery of a light beam;
a cartridge comprising a photonic sensor chip having a length axis and a width axis, wherein the photonic sensor chip comprises:
a plurality of grating couplers in a first areal portion of the photonic sensor chip;
a plurality of sensing sites; and
waveguides connecting each grating coupler of the plurality of grating couplers to a respective sensing site or group of sensing sites of the plurality of sensing sites; and
a cartridge holder for releasably receiving and locking the cartridge into a sensing position,
wherein the photonic sensor chip is aligned relative to the illumination module up to permitted alignment tolerances when the cartridge is locked into the sensing position,
wherein the alignment tolerances comprise:
a permitted amount of longitudinal misalignment along the length axis of the photonic sensor chip; and
a permitted amount of lateral misalignment along the width axis of the photonic sensor chip,
wherein the permitted amount of longitudinal misalignment and the permitted amount of lateral misalignment define a peripheral portion of the photonic sensor chip,
wherein the peripheral portion of the photonic sensor chip surrounds the first areal portion of the photonic sensor chip,
wherein the illumination module is arranged to project the light beam onto and illuminate a second areal portion of the photonic sensor chip when the cartridge is locked into the sensing position, and
wherein the second areal portion fully encompasses the first areal portion and at least a portion of the peripheral portion.

2. The sensing system of claim 1, wherein the alignment tolerances further comprise a permitted amount of angular misalignment, and wherein a light acceptance cone associated with each grating coupler of the plurality of grating couplers accommodates light beams projected onto the photonic sensor chip having angles of incidence within the permitted amount of angular misalignment.

3. The sensing system of claim 2, wherein the permitted amount of angular misalignment is at least +/−0.5° with respect to a nominal illumination angle for optimal coupling by the grating couplers of light beam projected onto the photonic sensor chip.

4. The sensing system of claim 1, wherein the plurality of grating couplers in the first areal portion form a grating coupler array, and wherein the peripheral portion of the photonic sensor chip extends over a distance of at least 20 μm at either side of the grating coupler array.

5. The sensing system of claim 1, wherein the plurality of grating couplers in the first areal portion form a two-dimensional grating coupler array, and wherein a separation distance between individual grating couplers of the two-dimensional grating coupler array is less than dimensions of the grating couplers along either of the length axis and the width axis of the photonic sensor chip.

6. The sensing system of claim 5, wherein the two-dimensional grating coupler array in the first areal portion extends over at least 20 μm in either direction of the first areal portion.

7. The sensing system of claim 1, wherein each grating coupler of the plurality of grating couplers is configured to couple a portion of the light beam projected onto the photonic sensor chip into a respective one of the waveguides in accordance with a coupling efficiency value, and wherein the coupling efficiency value of each grating coupler is between −60 dB and −10 dB within the permitted alignment tolerances.

8. The sensing system of claim 7, wherein a variance in the coupling efficiency values across the plurality of grating couplers is at most 10 dB in an absence of lateral misalignment and longitudinal misalignment.

9. The sensing system of claim 7, wherein a relative change in total coupled power related to the plurality of grating couplers when lateral misalignment or longitudinal misalignment is present is less than 10.0%.

10. The sensing system of claim 1, wherein the illumination module comprises a light source comprising a coherent laser.

11. The sensing system of claim 10, wherein the illumination module further comprises a collimator.

12. The sensing system of claim 1, wherein the illumination module is configured to deliver the light beam with a flat-top-shaped or Gaussian-shaped spatial beam profile.

13. The sensing system of claim 1, wherein the plurality of grating couplers is formed on a front side of the photonic sensor chip, and wherein the illumination module is arranged to illuminate the front side of the photonic sensor chip.

14. The sensing system of claim 1, further comprising a microfluidic delivery system formed in or over the cartridge, wherein the microfluidic delivery system comprises one or more fluidic channels overlaying or contacting the waveguides at the sensing sites, and wherein light propagating along the waveguides interacts with biological samples when the biological samples are delivered to the sensing sites via the fluidic channels.

15. The sensing system of claim 1, further comprising:
a plurality of light output couplers for coupling optical response signals from the sensing sites out of the photonic sensor chip; and
a readout module configured to detect the optical response signals.

16. The sensing system of claim 15, wherein each waveguide connecting one of the plurality of grating couplers to the respective sensing site or group of sensing sites is further connected to a power monitor.

17. A biomedical apparatus comprising:
a sensing system comprising:
an illumination module for delivery of a light beam;
a cartridge comprising a photonic sensor chip having a length axis and a width axis, wherein the photonic sensor chip comprises:
a plurality of grating couplers in a first areal portion of the photonic sensor chip;
a plurality of sensing sites; and
waveguides connecting each grating coupler of the plurality of grating couplers to a respective sensing site or group of sensing sites of the plurality of sensing sites; and
a cartridge holder for releasably receiving and locking the cartridge into a sensing position,
wherein the photonic sensor chip is aligned relative to the illumination module up to permitted alignment tolerances when the cartridge is locked into the sensing position,
wherein the alignment tolerances comprise:
a permitted amount of longitudinal misalignment along the length axis of the photonic sensor chip; and
a permitted amount of lateral misalignment along the width axis of the photonic sensor chip,
wherein the permitted amount of longitudinal misalignment and the permitted amount of lateral misalignment define a peripheral portion of the photonic sensor chip,
wherein the peripheral portion of the photonic sensor chip surrounds the first areal portion of the photonic sensor chip,
wherein the illumination module is arranged to project the light beam onto and illuminate a second areal portion of the photonic sensor chip when the cartridge is locked into the sensing position, and
wherein the second areal portion fully encompasses the first areal portion and at least a portion of the peripheral portion.

18. The biomedical apparatus of claim 17, wherein the alignment tolerances further comprise a permitted amount of angular misalignment, and wherein a light acceptance cone associated with each grating coupler of the plurality of grating couplers accommodates light beams projected onto the photonic sensor chip having angles of incidence within the permitted amount of angular misalignment.

19. The biomedical apparatus of claim 17, wherein the plurality of grating couplers in the first areal portion form a grating coupler array, and wherein the peripheral portion of the photonic sensor chip extends over a distance of at least 20 μm at either side of the grating coupler array.

20. A cartridge comprising:
a photonic sensor chip having a length axis and a width axis, wherein the photonic sensor chip comprises:
a plurality of grating couplers in a first areal portion of the photonic sensor chip;
a plurality of sensing sites; and
waveguides connecting each grating coupler of the plurality of grating couplers to a respective sensing site or group of sensing sites of the plurality of sensing sites; and
a cartridge holder for releasably receiving and locking the cartridge into a sensing position, wherein the photonic sensor chip is configured to be aligned relative to an illumination module up to permitted alignment tolerances when the cartridge is locked into the sensing position, wherein the alignment tolerances comprise:

a permitted amount of longitudinal misalignment along the length axis of the photonic sensor chip; and a permitted amount of lateral misalignment along the width axis of the photonic sensor chip, wherein the permitted amount of longitudinal misalignment and the permitted amount of lateral misalignment define a peripheral portion of the photonic sensor chip, wherein the peripheral portion of the photonic sensor chip surrounds the first areal portion of the photonic sensor chip, wherein a second areal portion of the photonic sensor chip is configured to be illuminated by the illumination module when the cartridge is locked into the sensing position, and wherein the second areal portion fully encompasses the first areal portion and at least a portion of the peripheral portion.

* * * * *